United States Patent
Randive et al.

[11] Patent Number: 6,159,446
[45] Date of Patent: Dec. 12, 2000

[54] HIGH MOISTURE TOOTHPASTE

[75] Inventors: Vinayak Bhalchandra Randive, Maharashtra; Vijay Kamalakant Gadkari, Bombay, both of India

[73] Assignee: FMC Corporation, Philadelphia, Pa.

[21] Appl. No.: 09/071,947

[22] Filed: May 4, 1998

[51] Int. Cl.$^7$ .................................................. A61K 7/16
[52] U.S. Cl. ............................................................ 424/49
[58] Field of Search ........................................ 424/49–58

[56] References Cited

U.S. PATENT DOCUMENTS

| | | | |
|---|---|---|---|
| 4,029,760 | 6/1977 | De Roeck | 424/47 |
| 4,140,757 | 2/1979 | Wason et al. | 424/49 |
| 4,340,583 | 7/1982 | Wason | 424/52 |
| 4,457,908 | 7/1984 | Scott | 424/49 |
| 4,565,692 | 1/1986 | Mulvey et al. | 424/49 |
| 4,601,280 | 7/1986 | Witzel | 126/121 |
| 4,645,662 | 2/1987 | Nakashima | 424/52 |
| 4,701,319 | 10/1987 | Woo | 424/52 |
| 4,702,905 | 10/1987 | Mitchell | 535/49 |
| 4,814,160 | 3/1989 | Carter et al. | 424/7.1 |
| 4,826,675 | 5/1989 | Gaffar et al. | 424/52 |
| 4,894,220 | 1/1990 | Nabi et al. | 424/49 |
| 5,002,934 | 3/1991 | Norton et al. | 424/49 |
| 5,094,839 | 3/1992 | Lowder et al. | 424/49 |
| 5,096,699 | 3/1992 | Gaffar et al. | 424/49 |
| 5,208,009 | 5/1993 | Gaffar et al. | 424/49 |
| 5,236,696 | 8/1993 | Catiis et al. | 424/49 |
| 5,296,214 | 3/1994 | Gaffar | 424/49 |
| 5,365,615 | 11/1994 | Piszkin | 2/422 |
| 5,468,489 | 11/1995 | Sarumarty | 424/47 |
| 5,496,541 | 3/1996 | Cutler | 424/49 |
| 5,531,982 | 7/1996 | Gaffner | 424/47 |
| 5,582,816 | 12/1996 | Mandanas et al. | 424/49 |
| 5,788,951 | 8/1998 | Blake-Haskins | 424/49 |

FOREIGN PATENT DOCUMENTS

| | | |
|---|---|---|
| 0 1129 001 | 5/1989 | Japan . |
| 10-025303 | 1/1998 | Japan . |

OTHER PUBLICATIONS

Chemical Abstracts 90: 174,532$_y$ (1979) –Abstract of JP 54/011,243 (1979).

*Primary Examiner*—Shep K. Rose
*Attorney, Agent, or Firm*—Bruce M. Monroe; Robert L. Andersen; Patrick C. Baker

[57] ABSTRACT

A stable, high moisture toothpaste has now been developed that comprises a carrageenan binder that is at least 70% iota carrageenan, a calcium based-polishing agent, humectant, surfactant, water and optional additives and therapeutic actives used in dentrifice compositions. The calcium-based agent is present at a weight percent concentration in the range of about 35 to 50, the water is about 35 to 50%, the humectant is about 5 to 15%, the carrageenan is about 0.5 to 0.85%, and the surfactant is about 0.5 to 5%. The high moisture, low cost toothpaste that is provided has favorable physical properties such as good viscosity and stability without the need for additional binder which is optional.

19 Claims, No Drawings

HIGH MOISTURE TOOTHPASTE

This invention pertains to stable, high water content dentifrice compositions comprising a carrageenan binder, a calcium based-polishing agent, humectant, surfactant, water and optional additives and therapeutic actives used in dentrifice compositions. More particularly, this invention pertains to a stable, high water content toothpaste where the weight percent of the polishing agent is in the range of 35 to 50%, the water is 35 to 50%, the humectant is 5 to 15%, the carrageenan is 0.5 to 0.85%, and at least 70% of the carrageenan content is iota carrageenan.

BACKGROUND

Toothpastes typically contain the following general types of ingredients: a polishing agent or abrasive, humectant, binder or thickener, surfactant, and water. The humectant and water are also referred to collectively as the vehicle. In addition, agents that provide therapeutic or cosmetic benefits may be incorporated such as preservatives, fluorides, flavoring agents, sweeteners and tartar control agents. Toothpaste formulations may vary widely in the specific types of ingredients and the amounts of these ingredients that are employed. Very broadly toothpastes contain 0.1 to 8% (weight percent) binder also frequently termed thickener or gelling agent, 5 to 70% water, 2 to 70% humectant, 5 to 50 weight percent polishing agent, 0.2 to 20% surfactant and 0.1 to 25% other ingredients or adjuvants such as flavoring, sweetening, fluorides, anti-tartars, preservatives, anti-calculus agents and other therapeutic actives compatible with toothpastes.

For consumer satisfaction, toothpaste formulations should possess certain excellent physical properties to which the consumer is accustomed. These properties provide a toothpaste that has appealing taste, has good cleansing effect, is easy to rinse, has excellent mouth feel, and has physical stability. Toothpastes with acceptable physical stability do not readily harden on the shelf and do not exhibit phase separation such as water or flavor separation. The appearance of the paste as it comes out of the dispenser is also considered important. It should appear smooth and have a pleasant sheen or glossy appearance.

Carrageenan is known to be an effective binder for providing toothpaste formulations with the aforementioned desirable properties. The carrageenans form gels that are thixotropic. Such gels are reported to exhibit excellent extrudability, flavor release and rinsability. The use of kappa and iota carrageenan as binders in gel toothpaste is known to also provide a toothpaste that is non-stringy.

The generic term carrageenan is applied to dozens of similar polysaccharides derived from seaweed. All carrageenans contain repeating galactose units joined by alternating $\beta 1 \rightarrow 3$ and $\alpha 1 \rightarrow 4$ glycosidic linkages and are partially sulfated. The types of carrageenans may be distinguished, in part, by their degree of sulfation. Kappa carrageenan has a repeating unit of D-galactose-4-sulfate-3,6-anhydro-D-galactose providing a sulfate ester content of about 18 to 25%. Iota carrageenan has a repeating unit of D-galactose-4-sulfate-3,6-anhydro-D-galactose-2-sulfate providing a sulfate ester content of about 25 to 34%. Lambda carrageenan has a repeating unit of D-galactose-2-sulfate-D-galactose-2,6-disulfate providing a sulfate ester content of about 30 to 40%.

Ideally, the above-mentioned excellent physical properties are provided in a toothpaste that is cost effective for the consumer. There is a continuing demand to provide toothpastes at lower cost while maintaining desirable properties. This is especially important in those parts of the world where, despite its well-established benefits in dental hygiene, toothpaste is still unaffordable. One approach to lower toothpaste cost is to seek low cost replacements for specific high cost ingredients. Carrageenan, for example, is a relatively expensive ingredient. Carrageenan can sometimes be used in lesser amounts when mixed with gums and other thickeners such as carboxymethylcellulose and xanthan. U.S. Pat. No. 4,140,757 describes replacing part of the carrageenan binder in a toothpaste formulation with a less expensive synthetic amorphous silicon dioxide thickener. In cases where part of the carrageenan is replaced with other binders, oftentimes the total binder concentration must be greater than when carrageenan is used as the sole binder.

Another approach to lower toothpaste cost is to provide toothpaste with higher water content. Generally, high water content toothpastes (or high moisture toothpastes) may be expected to be less expensive due to the low expense of water relative to the other ingredients. Water content in toothpastes have been reported to vary between 5 and 70 weight percent, but most toothpastes have a water content between about 10 and 25 weight percent.

Obtaining a high moisture toothpaste having the desired physical properties is a challenge. Relatively high water content is often associated with problems of low viscosity and/or phase separation. During storage water has a tendency to move downward and oils, such a flavorings, move upward. With high moisture toothpaste, the consumer may notice "wet cap" or flavor concentration in the tip depending on whether filled tubes were stored with the caps up or down. Separation may also adversely affect the sheen or gloss of the extruded paste.

High moisture toothpastes with carrageenan are known. The following U.S. patents describe various toothpaste formulations comprising carrageenan as a binder and a water content of greater than about 30% by weight: 4,340,583, 4,814,160, 4,826,675, 5,096,699, 5,208,009, and 5,356,615. High moisture toothpastes containing carrageenan are generally formulated with humectants that are present in greater than 20 weight percent and/or with the use of more or additional thickeners.

It is an object of this invention to develop a high moisture toothpaste with favorable physical properties comprising a toothpaste formulation where carrageenan is present in a concentration of no greater than about 0.85% and the total humectant concentration is no greater than about 15%. It is a further object to provide such a formulation that has favorable physical properties without the need for additional binder.

SUMMARY OF THE INVENTION

A stable, high moisture toothpaste has now been developed that comprises a carrageenan binder, a calcium-based polishing agent, humectant, surfactant, water and optional additives and therapeutic actives used in dentrifice compositions. The calcium-based polishing agent is present at a weight percent concentration in the range of about 35 to 50, the water is about 35 to 50%, the humectant is about 5 to 15%, the surfactant is about 0.5 to 5%, the carrageenan is about 0.5 to 0.85%, and at least 70% of the carrageenan content is iota carrageenan. The high moisture toothpaste that is provided has favorable physical properties such as good viscosity and stability without the need for additional binder which is optional.

DETAILED DESCRIPTION OF THE INVENTION

The present invention provides stable, high moisture content, low cost dentrifice compositions having an excellent balance of properties comprising about 0.5 to 0.85 weight percent carrageenan, at least 70% of which is iota carrageenan, about 35 to 50 weight percent water, about 35 to 50 weight percent of a calcium based polishing agent or abrasive, about 5–15 weight percent humectant, and about 0.5 to 5 weight percent surfactant. Optional ingredients that may be present include silica up to about 5 percent by weight and small amounts, 0.5 to 3.0 weight percent, of additional adjuvants such as flavors, preservatives, sweeteners, fluorides, anti-tartars, anticalculus and other therapeutic actives compatible with the dentrifice of this invention. The percentages of ingredients used in this specification refer to the weight percent of pure ingredient in the toothpaste, unless otherwise indicated.

In one embodiment of the invention, the weight percent of carrageenan is in the range of about 0.55 to 0.65. In this embodiment, a preferred weight percent of water is in the range of about 36 to 50, more preferably 36 to 46, a preferred weight percent of humectant is about 7 to 14, and a preferred weight percent of polishing agent is about 40 to 46, more preferably about 43 to 46.

In another embodiment of the invention, the weight percent of carrageenan is in the range of about 0.70 to 0.80. In this embodiment, a preferred weight percent of water is in the range of about 40 to 50, a preferred weight percent of humectant is about 7 to 14, and a preferred weight of polishing agent is about 40 to 46, more preferably about 40 to 43.

Many of the past problems of high moisture toothpastes are overcome by the compositions of this invention. They exhibit good Cuban values (have a good consistency) and have stability from flavor or water separation and hardening over extended time periods. In addition to good shelf life, the toothpastes have smoothness and a pleasant sheen or glossy appearance. These favorable properties have been achieved in a relatively low cost formulation, due in large part to the low levels of humectant that are required.

The high moisture toothpastes of this invention require iota carrageenan as the principal carrageenan component. The iota carrageenan is at least 70% by weight of the carrageenan, preferably at least 90%. Small amounts (less than 30% by weight) of other carrageenans, preferably kappa, may be used with iota carrageenan in this invention. The carrageenan usually contains a mixture of cations associated with the sulfate groups of the carrageenan such that the carrageenan is provided in a partial salt form. The cations are alkali metal and alkaline earth metal cations, such as sodium, potassium and calcium. It is preferred that about 9 to 12 percent of the iota carrageenan be in salt form, preferably as the sodium and potassium salts, with a minimum amount, less than about one percent, as the calcium salt of iota carrageenan. It is also preferred that the carrageenan be a medium or high viscosity carrageenan. The viscosity descriptions used herein refer to a 1.5% solution of carrageenan in water at 75° C. The term "high viscosity" means having a water viscosity of at least about 50 cps, "medium viscosity" means having a water vicosity of about 40 to 50 cps, and "low viscosity" means having a water viscosity of less than 40 cps. A preferred carrageenan for use in toothpastes of this invention is available from FMC Corporation under the name Viscarin®TP 399. Another preferred carrageenan is available from FMC under the name Viscarin®TP 329. The weight percent of carrageenan is in the range of about 0.5 to 0.85%. A preferred weight percent of carrageenan is in the range of about 0.55 to 0.80%. The carrageenan may be used with small amounts (0 to 0.50 weight percent) of other binders, such as other carrageenans, carboxymethyl cellulose, sodium carboxymethyl cellulose hydroxyethylcarboxyethyl cellulose, polyvinyl pyrrolidone, gum tragacanth, hydroxypropylmethyl cellulose, ethyl cellulose, starch, starch glycolate, polyvinyl alcohol, sodium alginate, carob bean gum and hydrophilic colloidal hydroxyvinyl polymers, such as Carbopols® to produce the high moisture toothpaste.

The usual vehicles of dentifrices are water and one or more humectants. The water used in this toothpaste can be any hygienically clean water such as tap water, well water, and spring water. The water is often deionized prior to use. Suitable humectants are the known lower straight chain or cyclic polyols of 3 to 6 carbons and mixtures there of. Preferred humectants are glycerol and sorbitol. Sorbitol was used as a 70% solution in water, which is a readily available form of sorbitol. The percentages of humectant such as sorbitol refer to the pure humectant in the toothpaste, unless otherwise noted. A preferred weight percent of sorbitol is in the range of about 7 to 14%. It is well known to employ glycerol-sorbitol mixtures. When using such a mixture, a preferred amount of glycerol is about 0 to 7 percent by weight. Other liquid polyols may also be used, such as polyethylene glycols, mannitols, xylitols, other sugar alcohols and polyoxyethylene alcohols. It is an advantage of this invention that high levels of humectant are not required in the high water formulation to compensate for the low binder concentration.

The calcium-based polishing agents of this invention include the calcium-based agents known to be useful in toothpastes. These are powdered materials having no or very low water solubility and a preferred particle size of about 1 to 40 microns in diameter, more preferably between about 2 to 20 microns in diameter, with normal particle size distributions. All such agents have polishing activity without being objectionably abrasive. Examples of suitable calcium-based polishing agents include dicalcium phosphate, tricalcium phosphate, calcium carbonate, calcium pyrophosphate, calcium silicate, and calcium aluminate. These polishing agents may be used with other abrasives such as crystalline silica, colloidal silica, complex aluminosilicates, aluminum hydroxide (including alumina trihydrate), magnesium phosphate, magnesium carbonate, bentonite, talc, aluminum oxide, aluminum silicate and silica xerogels. A preferred calcium-based polishing agent is precipitated chalk (calcium carbonate).

The surfactants (detergents) that may be used in the toothpaste of this invention are those commonly used to emulsify or otherwise uniformly disperse toothpaste components. It is generally preferred that the detergent be anionic or nonionic or a mixture thereof. Suitable types of anionic detergents include sodium lauryl sulfate, fatty acid monoglyceride sulfates, fatty alkyl sulfates, higher alkyl aryl sulfonates, higher alkyl sulfoacetates, higher olefin sulfonates, higher aliphatic acylamides of lower aliphatic aminocarboxylic acids, higher alkyl poly-lower alkoxy (of 3 to 100 alkoxy groups) sulfates, and fatty acid soaps. Examples of these anionic detergents include sodium lauryl sulfate, sodium hydrogentated coconut oil fatty acids monoglyceride monosulfate, sodium N-lauroyl sarcoside, and sodium cocate. Suitable types of nonionic detergents include chains of lower alkyene oxides such as ethylene oxide and propylene oxide.

Additional materials that are optionally added include flavorings, enamel hardening agents, and antibacterial compounds. Examples of flavoring materials include the sweetener saccharin, essential oils such as spearmint, peppermint, wintergreen, eucalyptus, lemon and lime. Examples of hardening agents include sodium monofluorophosphate, sodium fluoride and stannous fluoride. Examples of antibacterials are sodium benzoate and methyl or ethyl parasept.

The high moisture toothpastes of this invention may be prepared by batch or continuous manufacturing processes. A continuous process that may be used to manufacture toothpaste of this invention is described in U.S. Pat. No. 5,236,696 (Catiis et al.).

EXAMPLES

The toothpaste formulations in the following examples were prepared by either a hot process or an ambient temperature process. The hot process was performed according to the following steps: (1) The binder was dispersed into the humectant with a high speed stirrer and stirred for 10 minutes to form a gel. (2) The water was heated to 80° C. and added to the humectant and the stirring continued for 15 minutes while maintaining the temperature between 65 and 70° C. (3) The sodium saccharine and sodium benzoate were dry blended. The dry blend was stirred into the binder slurry and stirred for 15 minutes while maintaining the temperature between 65 and 70° C. (4) The gel (elixir) was transferred to a low speed Ross mixer with a vacuum attachment. A ROSS™ Mixer is a well known double planetary gear, two paddle mixer which operates at 20 to 100 revolutions per minute and can be operated under vacuum. (5) The chalk and optionally some silica was added to the elixir and mixed for 15 minutes under vacuum (at least 720 mm Hg.). (6) Flavoring was added to the elixir and mixed for 10 minutes in the Ross mixer under full vacuum. (7) The surfactant and sodium lauryl sulfate were added to the mix and mixing was continued under vacuum for 20 minutes. (8) A sample was withdrawn for testing and the batch discharged for filling.

The ambient temperature process is the same as the "Hot Process" procedure except that in steps (2) and (3) the temperature employed is ambient temperature. Numerous runs or experimental batches were conducted using either the Hot or the Ambient Process described herein.

In the Tables below, Cgns A-D are iota carrageenans, each associated with cations that are predominantly sodium and potassium. Cgn A is a medium viscosity carrageenan, Cgn B is a high viscosity carrageenan, Cgn C has a viscosity range of 5 to 50 cps for a 1.5% solution at 75° C., and Cgn D is a low viscosity carrageenan that contains about 10% silica zeodent. "Cgn E" is kappa carrageenan extract, SCITP 105 is iota carrageenan sold by Shemburg and KPFX 8806 is high viscosity iota carrageenan sold by Copenhagen Pectin. CMC 7MF, CMC(9M31 F) Aqualon and Daicel are carboxymethylcellulose which are sold commercially.

Comparisons were made among a number of formulations with varying amounts of the different carrageenans, water, humectant and polishing agent. To evaluate the effect of the ingredients and their amounts on Cuban values and stability, other components of the formulation were kept constant. Table 1 shows the ingredients that were kept constant in one set of comparisons.

TABLE 1

Ingredients other than Cgn, Water, Polishing Agent and Humectant

| Ingredient | Percent |
| --- | --- |
| Sodium saccharin | 0.20 |
| Sodium benzoate | 0.30 |

TABLE 1-continued

Ingredients other than Cgn, Water, Polishing Agent and Humectant

| Ingredient | Percent |
| --- | --- |
| Flavor | 1.00 |
| Sodium lauryl sulfate | 2.00 |

Table 2 illustrates some of the formulations containing the ingredients in Table 1 and varying amounts of the carrageenan A, water, humectant and polishing agent. The formulations in Table 2 were prepared by the hot process described above. The term "sorbitol 70" refers to a 70% solution of sorbitol in water.

TABLE 2

Representative Toothpastes with Carrageenan A by Hot Process

| No. | Cgn A | Sorbitol 70 | Glycerin | Pr. Chalk | Water |
| --- | --- | --- | --- | --- | --- |
| 1 | 0.80 | 15.0 | — | 42.0 | 38.70 |
| 2 | 0.80 | 15.0 | — | 40.0 | 40.70 |
| 3 | 0.80 | 15.0 | — | 40.0 | 40.70 |
| 4 | 0.75 | 15.0 | — | 40.0 | 40.75 |
| 5 | 0.80 | 10.0 | — | 40.0 | 45.70 |
| 6 | 0.80 | 15.0 | — | 43.0 | 37.70 |
| 7 | 0.75 | 15.0 | — | 43.0 | 37.75 |
| 8 | 0.65 | 15.0 | — | 46.0 | 34.85 |
| 9 | 0.55 | 20.0 | — | 46.0 | 29.95 |
| 10 | 0.65 | 20.0 | — | 40.0 | 35.85 |
| 11 | 0.65 | 20.0 | — | 46.0 | 29.85 |
| 12 | 0.80 | 20.0 | — | 40.0 | 35.70 |
| 13 | 0.80 | 20.0 | — | 46.0 | 29.70 |
| 14 | 0.58 | 15.0 | — | 46.0 | 34.92 |
| 15 | 0.65 | 10.0 | — | 43.0 | 42.85 |
| 16 | 0.65 | 15.0 | — | 43.0 | 37.85 |
| 17 | 0.65 | — | 10.0 | 43.0 | 42.85 |
| 18 | 0.60 | — | 15.0 | 43.0 | 37.90 |

Table 3 illustrates some of the formulations containing the ingredients in Table 1 and varying amounts of carrageenan B, water, sorbitol and polishing agent. The formulations in Table 3 were prepared by the hot process described above.

TABLE 3

Representative Toothpastes with Cgn B by Hot Process

| No. | Cgn B | Sorbitol 70 | Pr. Chalk | Pr. Silica | Water |
| --- | --- | --- | --- | --- | --- |
| 19 | 0.65 | 15.00 | 46.00 | — | 34.85 |
| 20 | 0.80 | 10.00 | 40.00 | — | 45.70 |
| 21 | 0.60 | 15.00 | 46.00 | — | 34.90 |
| 22 | 0.60 | 15.00 | 46.00 | — | 34.90 |
| 23 | 0.60 | 15.00 | 45.00 | — | 35.90 |
| 24 | 0.60 | 15.00 | 44.00 | — | 36.90 |
| 25 | 0.55 | 15.00 | 46.00 | — | 34.95 |
| 26 | 0.55 | 15.00 | 45.00 | — | 35.95 |
| 27 | 0.55 | 15.00 | 44.00 | — | 36.95 |
| 28 | 0.70 | 15.00 | 40.00 | — | 40.80 |
| 29 | 0.55 | 15.00 | 43.00 | 2.00 | 35.95 |
| 30 | 0.55 | 20.00 | 43.00 | 2.00 | 30.95 |

Table 4 illustrates some of the formulations containing the ingredients in Table 1 and varying amounts of carrageenan B, water, sorbitol and polishing agent. The formulations in Table 4 were prepared by the ambient process described above.

TABLE 4

Representative Toothpastes with Cgn B by Ambient Process

| No. | Cgn B | Sorbitol 70 | Pr. Chalk | Pr. Silica | Water |
|---|---|---|---|---|---|
| 31 | 0.60 | 15.00 | 46.00 | — | 34.90 |
| 32 | 0.60 | 15.00 | 46.00 | — | 34.90 |
| 33 | 0.60 | 15.00 | 46.00 | — | 34.90 |
| 34 | 0.60 | 15.00 | 45.00 | — | 35.90 |
| 35 | 0.60 | 15.00 | 44.00 | — | 36.90 |
| 36 | 0.55 | 15.00 | 46.00 | — | 34.95 |
| 37 | 0.55 | 15.00 | 45.00 | — | 35.95 |
| 38 | 0.55 | 15.00 | 44.00 | — | 36.95 |
| 39 | 0.55 | 15.00 | 43.00 | 2.00 | 35.95 |
| 40 | 0.55 | 20.00 | 43.00 | 2.00 | 30.95 |
| 41 | 0.60 | 15.00 | 46.00 | — | 34.90 |

Table 5 illustrates some of the formulations containing the ingredients in Table 1 with different carrageenans. The formulations in Table 5 were prepared by the hot process described above.

TABLE 5

Toothpastes with Various Carrageenans

| No. | Carrageenan Type | % | Sorbitol 70 | Pr. Chalk | Water |
|---|---|---|---|---|---|
| 42 | Cgn C | 1.40 | 15.00 | 40.00 | 40.10 |
| 43 | SCI TP 105 | 0.80 | 15.00 | 40.00 | 40.70 |
| 44 | KPF X 8806 | 0.80 | 15.00 | 40.00 | 40.70 |
| 45 | Cgn D | 0.80 | 15.00 | 40.00 | 40.70 |
| 46 | Cgn D | 0.80 | 15.00 | 40.00 | 40.70 |
| 47 | Cgn D | 0.75 | 15.00 | 40.00 | 40.75 |
| 48 | Cgn D | 0.80 | 10.00 | 40.00 | 45.70 |
| 49 | Cgn D | 0.65 | 15.00 | 46.00 | 34.85 |
| 50[1] | Cgn E | 0.50 | 15.00 | 43.00 | 37.70 |

[1]Daicel CMC (0.30%) added to formulation

Table 6 illustrates some comparative low moisture formulations containing the ingredients in Table 1 and carrageenan A. The formulations in Table 6 were made with less water and more humectant and prepared by the hot process described above.

TABLE 6

Comparative Toothpastes with Low Water

| No. | Cgn A | Sorbitol 70 | Glycerin | Pr. Chalk | Water |
|---|---|---|---|---|---|
| 51 | 0.62 | — | 25.00 | 46.00 | 24.88 |
| 52 | 0.62 | 25.00 | — | 46.00 | 24.88 |
| 53 | 0.65 | 25.00 | — | 46.00 | 24.85 |

TEST RESULTS

For each of the formulations prepared, Cuban values and physical stability were measured.

Cuban test values are directly related to the viscosity of the toothpaste. In the Cuban test (also termed the "Rack" test), the paste is squeezed from a tube through a fixed orifice across a grid of parallel rods, increasingly spaced apart. The test results are expressed as the greatest space number (numbers are from 1–12) which represents the longest distance between rods that support the dentifrice ribbon without having it break. The rack is about 300 millimeters (mm) long and about 100 mm wide. The stainless steel rods are spaced at increasing distances apart starting at 3 mm between rods 1 and 2 (space number 1) and the distance between rods increases by 3 mm from rod to rod. Thus the distance between rods 2 and 3 is 6 mm, and the distance between the twelfth and thirteenth rod (space number 12) is 39 mm. Ratings of 1–2 and 9–12 are not acceptable, 3 and 8 are acceptable, 4–7 are good.

In performing the Cuban test, the following procedure is followed. (1) A nozzle is fixed to a toothpaste tube filled with a toothpaste to be tested. (2) The tube filled with test toothpaste and having the nozzle attached is held at an angle of 45° to the rack device. Pressure is applied at the bottom of the tube and a uniform ribbon of paste is squeezed from the tube. While the ribbon of paste is being extruded from the tube the tube is moved across the rack in a straight line as fast as possible. There is no time limit fixed to stretch the ribbon of paste over the rack. If the ribbon breaks before the entire rack is traversed, the procedure is repeated. (3) The ribbon is allowed to stand for 30 seconds. At that time, the point at which the ribbon breaks is recorded as the rack rating or Cuban value. (4) The test is performed five times and the average reading is recorded, rounding off to the nearest complete figure.

Stability tests were conducted by filling tubes with the sample paste. The tubes were capped and stored flat for 12 weeks at room temperature and at 50° C. After the 12 week exposure, a toothpaste ribbon of about 5 cm length was squeezed from the tube. The tube was then slit open and the ribbon and contents were evaluated for flavor and phase separation (syneresis). The separation of the flavoring and water phase at the tip of the toothpaste tube may be noted as "wet cap". Flavor separation was rated as 0=none, 1=slight, 2=moderate and 3=severe. Stability was rated as "not ok", "ok", and "good". To be rated "not ok," the sample readily exhibited some undesirable properties such as flavor separation, syneresis, being very hard in the tube, or having unacceptable Cuban values. To be rated "ok," the sample did not separate but could be somewhat grainy and lacking in good sheen. To be rated "good," the sample exhibited no separation of any sort and the sample was superior in subtle details such as fine texture or not grainy and had superior sheen or gloss.

Table 7 shows the results of the Cuban and stability testing for the formulations described above in Tables 1–6.

TABLE 7

Test Results

| No. | Cuban Value | Stability RT | Stability 50° C. |
|---|---|---|---|
| 1 | 9 | ok | — |
| 2 | 7 | ok | ok |
| 3 | 7 | ok | ok |
| 4 | 7 | good | ok |
| 5 | 7 | ok | ok |
| 6 | 10 | good | good |
| 7 | 8 | ok | ok |
| 8 | 8 | ok | ok |
| 9 | 5 | ok | ok |
| 10 | 6 | ok | ok |
| 11 | 6 | ok | ok |
| 12 | 6 | good | good |
| 13 | 9 | ok | ok |
| 14 | 5 | not ok | not ok |
| 15 | 5 | ok | ok |
| 16 | 5 | ok | ok |
| 17 | 4 | ok | ok |
| 18 | 4 | good | good |
| 19 | 9 | good | good |
| 20 | 9 | ok | ok |
| 21 | 8 | ok | ok |
| 22 | 8 | — | not ok |
| 23 | 5 | — | ok |
| 24 | 5 | — | ok |
| 25 | 6 | good | good |

TABLE 7-continued

Test Results

| No. | Cuban Value | Stability RT | Stability 50° C. |
|---|---|---|---|
| 26 | 5 | not ok | — |
| 27 | 5 | ok | ok |
| 28 | 6 | good | good |
| 29 | 4 | ok | ok |
| 30 | 4 | ok | ok |
| 31 | 6 | ok | ok |
| 32 | 4 | ok | ok |
| 33 | 6 | ok | ok |
| 34 | 5 | good | good |
| 35 | 5 | good | good |
| 36 | 5 | good | good |
| 37 | 5 | good | good |
| 38 | 5 | good | good |
| 39 | 4 | ok | ok |
| 40 | 4 | ok | ok |
| 41 | 6 | — | ok |
| 42 | 6 | not ok | not ok |
| 43 | 7 | not ok | not ok |
| 44 | 3 | not ok | not ok |
| 45 | 5 | ok | — |
| 46 | 5 | not ok | not ok |
| 47 | 4 | not ok | not ok |
| 48 | 5 | not ok | not ok |
| 49 | 5 | not ok | not ok |
| 50 | 4 | not ok | not ok |
| 51 | 5 | good | good |
| 52 | 5 | good | good |
| 53 | 5 | ok | ok |

In some of the samples flavor separation occurred inside the tube. Those formulations that had more than slight separation (a rating of 2–3) are listed in Table 8.

TABLE 8

Toothpastes Exhibiting a Moderate to Severe Flavor Separation

| Flavor Separation Rating | Sample Numbers |
|---|---|
| 2 | 22, 46 |
| 3 | 42, 43, 44, 47, 48, 49, 50 |

As shown in Table 7 a number of formulations of this invention exhibit an acceptable Cuban value and a stability rating that is "ok" or "good." These desirable physical properties have been achieved in high water toothpaste formulations with relatively low concentrations of binder and humectant. It is apparent that various modifications may be made in the formulations of the present invention without departing from the inventive concepts herein, as defined in the claims.

What is claimed:

1. A toothpaste composition consisting essentially of:
   about 0.5 to 0.85 weight percent of a binder;
   about 35 to 50 weight percent water;
   about 35 to 50 weight percent of a calcium based polishing agent or abrasive;
   about 5–15 weight percent humectant;
   about 0.5 to 5.0 weight percent surfactant; and
   optionally, one or more additional materials selected from the group consisting of flavoring materials, enamel hardening agents, and antibacterial compounds;
   in which:
   the binder consists essentially of carrageenan;
   at least 70% of the carrageenan is medium or high viscosity iota-carrageenan; and
   the composition has a Cuban value in the range of 3 to 8.

2. The toothpaste composition of claim 1 in which the polishing agent is selected from precipitated chalk and dicalcium phosphate.

3. The toothpaste composition of claim 1 in which the humectant is sorbitol, glycerin or a mixture thereof.

4. The toothpaste composition of claim 1 in which the surfactant is sodium lauryl sulfate.

5. The toothpaste composition of claim 1 in which the carrageenan is in a partial salt form in which about 9 to 12 percent of the iota-carrageenan is present as the sodium and potassium salts and less than 1 percent is present as the calcium salt.

6. The toothpaste composition of claim 1 in which at least 90% of the carrageenan is medium or high viscosity iota-carrageenan.

7. The toothpaste composition of claim 6 in which the polishing agent is precipitated chalk, the surfactant is sodium lauryl sulfate, and the humectant is sorbitol.

8. The toothpaste composition of claim 7 in which the carrageenan is in a partial salt form in which about 9 to 12 percent of the iota-carrageenan is present as the sodium and potassium salts and less than 1 percent is present as the calcium salt.

9. The toothpaste composition of claim 1 in which the weight percent of carrageenan is about 0.55 to 0.80, the weight percent of water is about 36 to 50, the weight percent of calcium based polishing agent is about 40 to 46, and the weight percent of humectant is about 7 to 14.

10. The toothpaste composition of claim 9 in which at least 90% of the carrageenan is medium or high viscosity iota-carrageenan.

11. The toothpaste composition of claim 10 in which the carrageenan is in a partial salt form in which about 9 to 12 percent of the iota-carrageenan is present as the sodium and potassium salts and less than 1 percent is present as the calcium salt.

12. The toothpaste composition of claim 11 in which the weight percent of carrageenan is about 0.55 to 0.65, the weight percent of water is about 36 to 46, the weight percent of calcium based polishing agent is about 43 to 46.

13. The toothpaste composition of claim 12 in which at least 90% of the carrageenan is medium or high viscosity iota-carrageenan.

14. The toothpaste composition of claim 13 in which the carrageenan is in a partial salt form in which about 9 to 12 percent of the iota-carrageenan is present as the sodium and potassium salts and less than 1 percent is present as the calcium salt.

15. The toothpaste composition of claim 11 in which the weight percent of carrageenan is about 0.70 to 0.80, the weight percent of water is about 40 to 50, the weight percent of based polishing agent is about 40 to 43.

16. The toothpaste composition of claim 13 in which at least 90% of the carrageenan is medium or high viscosity iota-carrageenan.

17. The toothpaste composition of claim 16 in which the carrageenan is in a partial salt form in which about 9 to 12 percent of the iota-carrageenan is present as the sodium and potassium salts and less than 1 percent is present as the calcium salt.

18. The toothpaste composition of claim 11 in which a flavoring material, an enamel hardening agent, an antibacterial compound or a combination thereof is present.

19. The toothpaste composition of claim 16 in which a flavoring material, an enamel hardening agent, an antibacterial compound or a combination thereof is present.

* * * * *